US012616520B2

(12) United States Patent
Vadali et al.

(10) Patent No.: US 12,616,520 B2
(45) Date of Patent: May 5, 2026

(54) MAGNETIC AUTO-ALIGNMENT CONNECTOR

(71) Applicant: Covidien LP, Mansfield, MA (US)

(72) Inventors: K V S Manoj Kumar Vadali, Hyderabad (IN); Joseph D. Brannan, Lyons, CO (US); Venkata Prasad Mooram, Hyderabad (IN)

(73) Assignee: Covidien LP, Mansfield, MA (US)

( * ) Notice: Subject to any disclaimer, the term of this patent is extended or adjusted under 35 U.S.C. 154(b) by 392 days.

(21) Appl. No.: 18/038,510

(22) PCT Filed: Nov. 3, 2021

(86) PCT No.: PCT/US2021/057799
§ 371 (c)(1),
(2) Date: May 24, 2023

(87) PCT Pub. No.: WO2022/115214
PCT Pub. Date: Jun. 2, 2022

(65) Prior Publication Data
US 2024/0016542 A1 Jan. 18, 2024

Related U.S. Application Data

(60) Provisional application No. 63/119,038, filed on Nov. 30, 2020.

(51) Int. Cl.
*A61B 18/18* (2006.01)

(52) U.S. Cl.
CPC .. *A61B 18/1815* (2013.01); *A61B 2018/1823* (2013.01)

(58) Field of Classification Search
CPC .................... A61B 18/1815; A61B 2018/1823
See application file for complete search history.

(56) References Cited

U.S. PATENT DOCUMENTS 9,196,979 B2 * 11/2015 Kim ........................ H01R 13/64
9,640,921 B2 * 5/2017 Choi .................. H01R 13/6683
(Continued)

OTHER PUBLICATIONS

International Search Report and Written Opinion dated Feb. 3, 2022, issued in corresponding international application No. PCT/US2021/057799, 13 pages.

*Primary Examiner* — Michael F Peffley
(74) *Attorney, Agent, or Firm* — Carter, DeLuca & Farrell, LLP

(57) ABSTRACT

A microwave ablation system includes a surgical instrument having an instrument connector and a microwave generator having a generator connector. The instrument connector includes a magnet and a plurality of conductors. The generator connector is configured to couple to the instrument connector and includes a housing, a support base, a magnet, at least one spring, and a plurality of pogo pins. The support base is operably coupled to the housing and configured to move longitudinally along a longitudinal axis of the generator connector. The magnet is operably coupled to the support base and positioned to align with the magnet of the instrument connector. The spring is configured to bias the support base proximally within the housing. The pogo pins extend distally from the support base with each pogo pin being configured to align with a respective conductor of the plurality of conductors of the instrument connector.

20 Claims, 3 Drawing Sheets

(56)     References Cited

U.S. PATENT DOCUMENTS

| | | | | |
|---|---|---|---|---|
| 10,363,098 B2 * | 7/2019 | Brannan | ................ | A61B 34/20 |
| 10,658,793 B2 * | 5/2020 | Blake | ........................ | G06F 1/18 |
| 11,045,223 B2 * | 6/2021 | Beaupre | .................. | A61N 7/00 |
| 11,051,875 B2 * | 7/2021 | Hubelbank | .......... | A61B 18/148 |
| 2016/0141809 A1 | 5/2016 | Choi | | |
| 2017/0265941 A1 | 9/2017 | Brannan et al. | | |
| 2018/0206884 A1 | 7/2018 | Beaupre | | |
| 2023/0420884 A1 * | 12/2023 | Do | ..................... | H01R 13/6205 |

\* cited by examiner

MAGNETIC AUTO-ALIGNMENT CONNECTOR

CROSS-REFERENCE TO RELATED APPLICATIONS

This application claims the benefit of U.S. Provisional Patent Application Ser. No. 63/119,038, filed on Nov. 30, 2020.

FIELD

The present disclosure relates to magnetic auto-alignment connectors for a microwave generator and surgical instrument.

BACKGROUND

In microwave ablation, an electromagnetic field is used to heat and destroy tumor cells. Treatment may involve inserting an ablation probe into tissues where cancerous tumors have been identified. Once the ablation probe is properly positioned, the ablation probe induces an electromagnetic field within the tissue surrounding the ablation probe to ablate the tissue.

Typically, systems for microwave ablation procedures include a microwave generator and a microwave instrument such as an ablation probe having an antenna assembly. The microwave generator and microwave instrument are operatively coupled to each other by a coaxial cable for carrying microwave signals from the microwave generator to the microwave instrument. Microwave generators typically include circuitry for generating microwave signals and a controller for controlling the operation of the circuitry and controlling a user interface, such as a display. The user interface includes user controls for setting characteristics of the microwave signals, such as buttons for adjusting the power level of the microwave signals.

Misalignment or improper connection of the microwave instrument to the microwave generator can lead to damage to the microwave generator, the microwave instrument, or both.

SUMMARY

In accordance with aspects of the present disclosure, a microwave ablation system is provided. The microwave ablation system includes a surgical instrument having an instrument connector and a microwave generator having a generator connector. The instrument connector includes a magnet and a plurality of conductors. The generator connector is configured to couple to the instrument connector and includes a housing, a support base, a magnet, at least one spring, and a plurality of pogo pins. The support base is operably coupled to the housing and configured to move longitudinally along a longitudinal axis of the generator connector. The magnet is operably coupled to the support base and positioned to align with the magnet of the instrument connector. The at least one spring is configured to bias the support base proximally within the housing. The plurality of pogo pins extends distally from the support base with each pogo pin of the plurality of pogo pins being configured to align with a respective conductor of the plurality of conductors of the instrument connector.

In an aspect, the magnet of the generator connector is configured to cause the support base to move distally against the bias of the spring when the instrument connector is properly aligned with the generator connector and the instrument connector is in proximity to the generator connector.

In an aspect, distal movement of the support base causes each pogo pin of the plurality of pogo pins to advance distally relative to the housing and contact the respective conductor of the plurality of conductors.

In an aspect, the magnet of the generator connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

In an aspect, the magnet of the generator connector is a first generator magnet having a first polarity and the generator connector includes a second generator magnet having a second polarity. The first polarity and the second polarity may be opposite. Additionally, or alternatively, the magnet of the instrument connector is a first instrument magnet having a polarity opposite the first polarity of the first generator magnet and the instrument connector includes a second instrument magnet having a polarity opposite the second polarity of the second generator magnet.

In an aspect, the magnet of the instrument connector is a polymagnet defining a first polarity pattern and the magnet of the generator connector is a polymagnet defining a second polarity pattern configured to align with the first polarity pattern of the polymagnet of the instrument connector.

In an aspect, the surgical instrument includes a thermocouple and a microwave antenna and at least one of the plurality of conductors is operably coupled to at least one of the thermocouple, for example via a temperature sensing circuit, or the microwave antenna.

In accordance with another aspect of the present disclosure, a microwave generator is provided. The microwave generator is configured to couple to an instrument connector of a surgical instrument. The microwave generator includes a housing, a support base operably coupled to the housing and configured to move longitudinally along a longitudinal axis of the generator connector, a magnet operably coupled to the support base and positioned to align with a magnet of the instrument connector, at least one spring configured to bias the support base proximally within the housing, and a plurality of pogo pins extending distally from the support base. Each pogo pin of the plurality of pogo pins is configured to align with a respective conductor of a plurality of conductors of the instrument connector.

In an aspect, the magnet of the generator connector is configured to cause the support base to move distally against the bias of the spring when the instrument connector is properly aligned with the generator connector and the instrument connector is in proximity to the generator connector.

In an aspect, distal movement of the support base causes each pogo pin of the plurality of pogo pins to advance distally relative to the housing and contact the respective conductor of the plurality of conductors.

In an aspect, the magnet of the generator connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

In an aspect, the magnet of the generator connector is a first generator magnet having a first polarity and the generator connector includes a second generator magnet having a second polarity. The first polarity and the second polarity may be opposite. Additionally, or alternatively, the magnet of the generator connector is a polymagnet defining a polarity pattern configured to align with a polarity pattern of a polymagnet of the instrument connector.

In accordance with another aspect of the present disclosure a surgical instrument is provided and includes a microwave ablation antenna and an instrument connector. The instrument connector is operably coupled to the microwave ablation antenna and configured to operably couple to a generator connector of a microwave generator. The instrument connector includes a housing, a support base operably coupled to the housing and configured to move longitudinally along a longitudinal axis of the instrument connector, a magnet operably coupled to the support base and positioned to align with a magnet of the generator connector, at least one spring configured to bias the support base proximally within the housing, and a plurality of pogo pins extending distally from the support base. Each pogo pin of the plurality of pogo pins is configured to align with a respective conductor of a plurality of conductors of the generator connector.

In an aspect, the magnet of the instrument connector is configured to cause the support base to move distally against the bias of the spring when the instrument connector is properly aligned with the generator connector and the instrument connector is in proximity to the generator connector.

In an aspect, distal movement of the support base causes each pogo pin of the plurality of pogo pins to advance distally relative to the housing and contact the respective conductor of the plurality of conductors.

In an aspect, the magnet of the instrument connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 1:
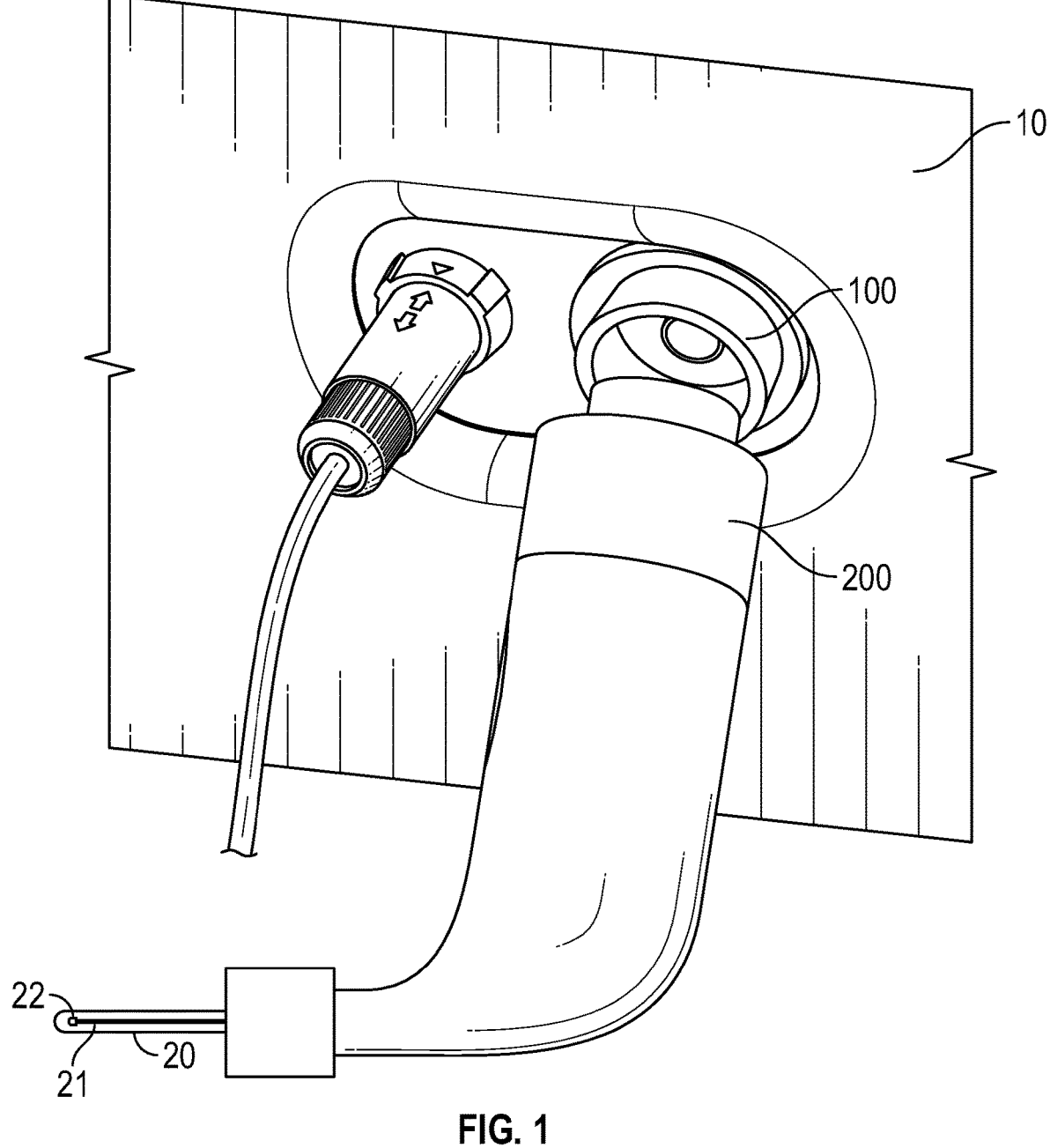
FIG. 1 is a perspective view of a generator connector and an instrument connector.

As shown in FIG. 1, the microwave ablation system generally includes a microwave generator 10 and a surgical instrument 20 configured to couple to the microwave generator 10. Although the surgical instrument 20 is illustrated and described as being configured to connect directly to the microwave generator 10, it is contemplated that the surgical instrument 20 may be connected to the microwave generator 10 by a reusable cable or other extension cable.

The surgical instrument 20 may include a device ID module having a device unique identification resistor ("DUIR") and a device ID memory. The DUIR has a device unique identification ("DUID") resistance that may be measured by the microwave generator 10 and compared to a resistance value indicator stored in memory of the microwave generator 10 to identify a type of the surgical instrument 20. Based on the identified type of the surgical instrument 20, a determination can be made as to whether or not the connected device is of the type that is compatible with the microwave generator 10. The device ID module may be incorporated within the surgical instrument 20 or may be incorporated within a separate connector or adapter configured to mate with a connector of an intermediate reusable cable.

The surgical instrument 20 may be a microwave ablation instrument including a microwave ablation antenna 22 for emitting microwave ablation energy to tissue generated from the microwave generator 10. Additionally, the surgical instrument 20 may include a thermocouple 21, which is coupled to a temperature measuring circuit, for measuring a temperature of portions of the surgical instrument 20 (e.g., the microwave ablation antenna 22) or tissue adjacent portions of the surgical instrument 20. The surgical instrument 20 includes an instrument connector 200 which is configured to connect to a generator connector 100 of the microwave generator 10.

Figure 2:
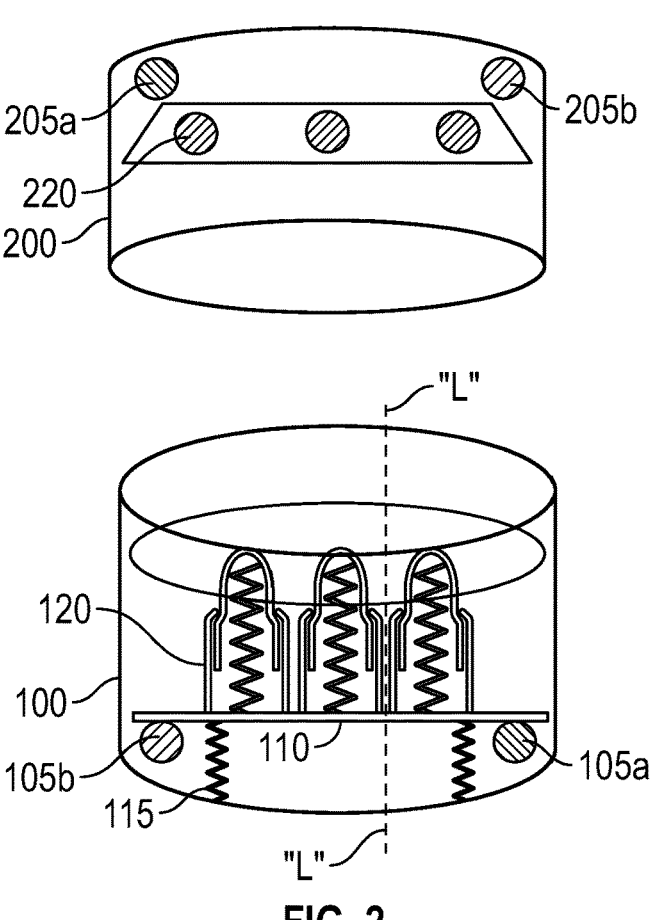
FIG. 2 is a block diagram of the generator connector spaced apart from, and properly aligned with, the instrument connector of FIG. 1.
Figure 3:
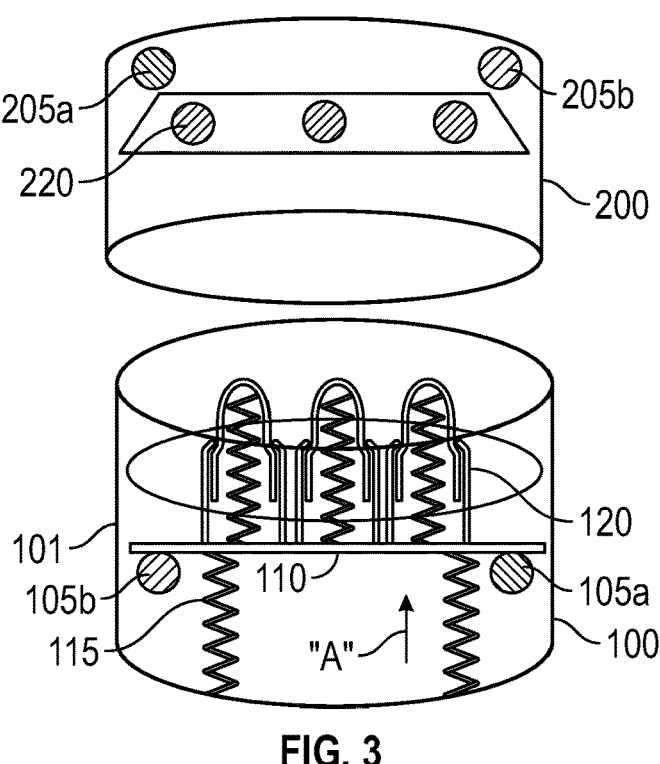
FIG. 3 is a block diagram of the generator connector in proximity to, and properly aligned with, the instrument connector of FIG. 1.
Figure 4:
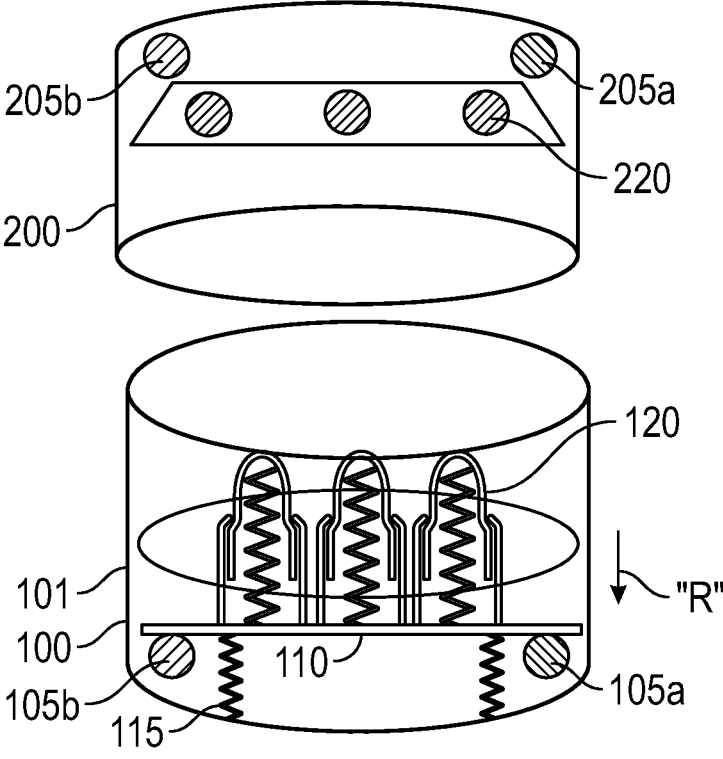
FIG. 4 is a block diagram of the generator connector in proximity to, and misaligned with, the instrument connector of FIG. 1.

FIGS. 2-4 illustrate the components of the instrument connector 200 of the surgical instrument 20 and the generator connector 100 of the microwave generator 10. Although the components are illustrated and described as being a component of one of the instrument connector 200 or the generator connector 100, it is appreciated that some or all of the components described as being included in the instrument connector 200 may instead be included in the generator connector 100 and vice versa. Additionally, or alternatively, while illustrated and described as being components of the instrument connector 200 and the generator connector 100, it is contemplated that some or all of the components may be embodied in an interconnecting intermediate cable.

The instrument connector 200 of the surgical instrument 20 includes at least one magnet, shown as magnet 205a and magnet 205b, and a plurality of conductors 220. Each of conductors 220 is configured to electrically connect a component of the surgical instrument 20 with a component of the microwave generator 10 when the surgical instrument 20 is properly coupled to the microwave generator.

The generator connector 100 includes a housing 101, a support base 110 operably coupled to an inner surface of the housing 101, at least one magnet, shown as magnet 105a and magnet 105b, at least one spring 115 operably coupled to the support base 110, and a plurality of pogo pins 120 extending distally from the support base 110. The support base 110 is movable longitudinally along a longitudinal axis "L" of the generator connector 100, between an outward state and an inward state. The spring 115 is coupled to the support base

110 and is biased to a compressed state to bias the support base 110 proximally to the inward state within the housing 101 of the generator connector 100. For example, the spring 115 may be coupled between a surface of the support base 110 and a surface of the housing 101. When an external force (e.g., an external magnetic attraction force) is applied to the support base 110, such external force stretched the spring 115 from the biased compressed state to a stretched state against the bias force of the spring 115.

Each of magnet 105a and magnet 105b is operably coupled to the support base 110 and is positioned to align with one of magnet 205a and magnet 205b of the instrument connector 200 when the instrument connector 200 is aligned with the generator connector 100. Additionally, each pogo pin of the plurality of pogo pins 120 is configured to align with a respective conductor of the plurality of conductors 220 of the instrument connector 200 when the instrument connector 200 is aligned with the generator connector 100. The plurality of pogo pins 120 of the generator connector 100 only form electrical contact with the plurality of conductors 220 of the instrument connector 200 when the instrument connector 200 is properly aligned with, and properly connected to, the generator connector 100. On the other hand, the plurality of pogo pins 120 of the generator connector 100 are prevented from forming electrical contact with the plurality of conductors 220 of the instrument connector 200 when the instrument connector 200 is improperly aligned with, and thus improperly connected to, the generator connector 100.

The magnet 105a and the magnet 105b of the generator connector 100 are configured to cause the support base 110 to move distally (e.g., outward), in the direction of arrow "A" (FIG. 3), causing the spring 115 to stretch from its resting compressed state against the bias of the spring 115 when the instrument connector 200 is properly aligned with the generator connector 100 and the instrument connector 200 is in proximity to the generator connector 100. Distal (e.g., outward) movement of the support base 110 in the direction of arrow "A" (FIG. 3) causes each pogo pin of the plurality of pogo pins 120 to advance distally relative to the housing 101 to contact the respective conductor of the plurality of conductors 220 of the instrument connector 200 when the instrument connector 200 is properly aligned with the generator connector 100 and the instrument connector 200 is in proximity to the generator connector 100.

Additionally, the magnet 105a and the magnet 105b of the generator connector 100 are configured to impart a magnetic force which causes the support base 110 to move proximally (e.g., inward), or otherwise remain in place thereby preventing its distal/outward movement, in the direction of arrow "R" (FIG. 4), with the bias of the spring 115, when the instrument connector 200 is improperly aligned with the generator connector 100 and the instrument connector 200 is in proximity to the generator connector 100. Such a configuration prevents the plurality of pogo pins 120 of the generator connector 100 from contacting the plurality of conductors 220 of the instrument connector 200. Such an arrangement ensures that no electrical contact can be made between the electrical components of the surgical instrument 20 and the microwave generator 10 when the instrument connector 200 of the surgical instrument 20 is improperly aligned or improperly connected to the generator connector 100 of the microwave generator 10, thereby avoiding any potential for damage to either or both of the microwave generator 10 and the surgical instrument 20.

In addition, when the instrument connector 200 is improperly aligned with, and brought in proximity to, the generator connector 100 a magnetic feedback is generated for the user indicating that the two components are not properly aligned. Additionally, the lack of an electrical connection between the instrument connector 200 and the generator connector 100 when the two are misaligned results in the microwave generator 10 generating a signal or notification (e.g., tactile, audible, and/or visual) that the surgical instrument 20 is not detected, or otherwise improperly connected to the microwave generator 10.

The magnet 105a of the generator connector 100 may have a first polarity which is opposite the polarity of the magnet 205b of the instrument connector 200 such that when the instrument connector 200 is properly aligned with the generator connector 100 and brought in proximity thereto, the magnet 105a and the magnet 205b are attracted to each other. Similarly, the magnet 105b of the generator connector 100 may have a second polarity which is opposite the polarity of the magnet 205a of the instrument connector 200 such that when the instrument connector 200 is properly aligned with the generator connector 100 and brought in proximity thereto, the magnet 105a and the magnet 205b are attracted to each other.

As illustrated in FIG. 3, The attraction between the reverse polarities of the magnet 105a and the magnet 205b (and likewise, the reverse polarities of the magnet 105b and the magnet 205a), along with the coupling of the magnet 105a and the magnet 105b to the movable support base 110, causes the support base 110 to move distally (e.g., outward) in the direction of arrow "A" relative to the housing 101. On the other hand, as shown in FIG. 4, when the instrument connector 200 is improperly aligned with the generator connector 100, the matching polarity of the magnet 105a with the magnet 205a, and likewise the matching polarity of the magnet 105b and the magnet 205b, generates a repelling force, thereby forcing the support base 110 to move proximally (e.g., inward) in the direction of arrow "R" with the compression bias of the spring 115 or to remain in the inward position. In one aspect, magnets 105a, 105b, 205a, and 205b are polymagnets defining corresponding polarity patterns to achieve the above-described attracting and repelling forces.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation system, comprising:
   a surgical instrument including an instrument connector, the instrument connector including a first magnet and a plurality of conductors; and
   a microwave generator including a generator connector configured to operably couple to the instrument connector, the generator connector including:
   a housing;
   a support base operably coupled to the housing and configured to move longitudinally along a longitudinal axis of the generator connector;
   a second magnet operably coupled to the support base and positioned to align with the first magnet of the instrument connector;

at least one spring configured to bias the support base proximally within the housing; and a plurality of pogo pins extending distally from the support base, wherein each pogo pin of the plurality of pogo pins is configured to align with a respective conductor of the plurality of conductors of the instrument connector.

2. The microwave ablation system according to claim 1, wherein the second magnet of the generator connector is configured to cause the support base to move distally against the bias of the spring when the instrument connector is properly aligned with the generator connector and the instrument connector is in proximity to the generator connector.

3. The microwave ablation system according to claim 1, wherein distal movement of the support base causes each pogo pin of the plurality of pogo pins to advance distally relative to the housing and contact the respective conductor of the plurality of conductors.

4. The microwave ablation system according to claim 1, wherein the second magnet of the generator connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

5. The microwave ablation system according to claim 1, wherein the second magnet of the generator connector has a first polarity and the generator connector includes a third magnet having a second polarity.

6. The microwave ablation system according to claim 5, wherein the first polarity and the second polarity are opposite.

7. The microwave ablation system according to claim 5, wherein the first magnet of the instrument connector has a polarity opposite the first polarity of the second magnet of the generator connector and the instrument connector includes a fourth magnet having a polarity opposite the second polarity of the third magnet of the generator connector.

8. The microwave ablation system according to claim 1, wherein the first magnet of the instrument connector is a polymagnet defining a first polarity pattern and the second magnet of the generator connector is a polymagnet defining a second polarity pattern configured to align with the first polarity pattern of the first magnet of the instrument connector.

9. The microwave ablation system according to claim 1, wherein the surgical instrument includes a thermocouple and a microwave antenna and at least one of the plurality of conductors is operably coupled to at least one of the thermocouple or the microwave antenna.

10. A microwave generator including a generator connector configured to operably couple to an instrument connector, the generator connector comprising:

a housing;

a support base operably coupled to the housing and configured to move longitudinally along a longitudinal axis of the generator connector;

a magnet operably coupled to the support base and positioned to align with a magnet of the instrument connector;

at least one spring configured to bias the support base proximally within the housing; and a plurality of pogo pins extending distally from the support base, wherein each pogo pin of the plurality of pogo pins is configured to align with a respective conductor of a plurality of conductors of the instrument connector.

11. The microwave generator according to claim 10, wherein the magnet of the generator connector is configured to cause the support base to move distally against the bias of the spring when the instrument connector is properly aligned with the generator connector and the instrument connector is in proximity to the generator connector.

12. The microwave generator according to claim 10, wherein distal movement of the support base causes each pogo pin of the plurality of pogo pins to advance distally relative to the housing and contact the respective conductor of the plurality of conductors.

13. The microwave generator according to claim 10, wherein the magnet of the generator connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

14. The microwave generator according to claim 10, wherein the magnet of the generator connector is a first generator magnet having a first polarity and the generator connector includes a second generator magnet having a second polarity.

15. The microwave generator according to claim 14, wherein the first polarity and the second polarity are opposite.

16. The microwave generator according to claim 10, wherein the magnet of the generator connector is a polymagnet defining a polarity pattern configured to align with a polarity pattern of a polymagnet of the instrument connector.

17. A surgical instrument, comprising:

a microwave ablation antenna; and an instrument connector operably coupled to the microwave ablation antenna and configured to operably couple to a generator connector of a microwave generator, the instrument connector including:

a housing;

a support base operably coupled to the housing and configured to move longitudinally along a longitudinal axis of the instrument connector;

a magnet operably coupled to the support base and positioned to align with a magnet of the generator connector;

at least one spring configured to bias the support base proximally within the housing; and a plurality of pogo pins extending distally from the support base, wherein each pogo pin of the plurality of pogo pins is configured to align with a respective conductor of a plurality of conductors of the generator connector.

18. The surgical instrument according to claim 17, wherein the magnet of the instrument connector is configured to cause the support base to move distally against the bias of the spring when the instrument connector is properly aligned with the generator connector and the instrument connector is in proximity to the generator connector.

19. The surgical instrument according to claim 17, wherein distal movement of the support base causes each pogo pin of the plurality of pogo pins to advance distally relative to the housing and contact the respective conductor of the plurality of conductors.

20. The surgical instrument according to claim 17, wherein the magnet of the instrument connector is configured to cause the support base to move proximally with the bias of the spring when the instrument connector is improperly aligned with the generator connector and the instrument connector is in proximity to the generator connector to prevent the plurality of pogo pins from contacting the plurality of conductors.

\* \* \* \* \*